United States Patent

Surburg et al.

[11] Patent Number: 5,874,398
[45] Date of Patent: Feb. 23, 1999

[54] ETHYLVANILLIN ISOBUTYRATE

[75] Inventors: Horst Surburg; Peter Esser; Steffen Sonnenberg; Arturetto Landi; Peter Wörner; Matthias Güntert, all of Holzminden; Gerhard Scheideler, Höxter, all of Germany

[73] Assignee: Haarmann & Reimer GmbH, Holzminden, Germany

[21] Appl. No.: 58,439

[22] Filed: Apr. 9, 1998

[30] Foreign Application Priority Data

Apr. 10, 1997 [DE] Germany .................. 197 14 826.3

[51] Int. Cl.$^6$ ..................................... A61K 7/46
[52] U.S. Cl. ...................... 512/21; 426/538; 131/276; 560/144

[58] Field of Search ................... 512/21; 426/538; 131/276; 560/144

[56] References Cited

U.S. PATENT DOCUMENTS 5,120,368  6/1992  Houminer et al. .................. 131/276
5,358,930  10/1994  Sprecker et al. .................... 512/21

*Primary Examiner*—Samuel Barts
*Attorney, Agent, or Firm*—Brinks Hofer Gilson & Lione

[57] ABSTRACT

Ethylvanillin isobutyrate is a valuable new fragrance and flavor substance which, because of its extraordinary organoleptic profile and its favorable technical properties, permits hitherto unknown effects in perfumery and flavoring.

10 Claims, No Drawings

ETHYLVANILLIN ISOBUTYRATE

BACKGROUND OF THE INVENTION

1. Field of the Invention

The invention relates to ethylvanillin isobutyrate I (=3-ethoxy-4-isobutyryloxy-benzaldehyde), to a process for its preparation and to its use as a fragrance and flavour substance.

2. Discussion of the Background

In the fragrance industry, it is a generally accepted fact that, for the preparation of perfume oils, there is an ongoing need for novel fragrances provided that they have additional positive secondary properties beyond their odoriferous properties, such as, for example, higher stability, lower tendency to form discolorations etc., or can replace those natural products in a perfume composition which are very expensive and are also frequently subject to severe price and quality fluctuations. The compound according to the invention, ethylvanillin isobutyrate, satisfies both criteria.

Vanillin (4-hydroxy-3-methoxybenzaldehyde) and ethylvanillin (3-ethoxy-4-hydroxy-benzaldehyde) are used on a large scale for the composition of perfume oils. They give perfumes an extraordinarily rich, potent sweetness. However, both compounds have the disadvantage that they decompose noticeably in alcoholic solution in daylight and as a result lead to disturbing brown-violet discolorations.

Vanillin derivatives, which are either obtainable commercially, such as vanillin isobutyrate, or are described in the literature, such as ethylvanillin propionate (U.S. Pat. No. 5,358,930), fall a long way short of the odour and flavour of natural vanillin, and even their solutions have—at least in some cases—a disturbing tendency to decompose in daylight. There was thus a need for a product which overcomes the disadvantages of the prior art.

SUMMARY OF THE INVENTION

Surprisingly, ethylvanillin isobutyrate is, with respect to its organoleptic properties, markedly superior to the vanillin and ethylvanillin derivatives known to date, both as regards the strength and also the nature of the organoleptic impression. It has a sweet natural vanilla-type odour and flavour which is very reminiscent of expensive real vanilla pod extract, coupled with a very appetizing buttery-creamy chocolate note. As well as being used in perfume oils, the compound according to the invention is thus also particularly well suited for flavouring foodstuffs, such as, for example, ice cream or desserts.

DESCRIPTION OF THE INVENTION

Compared to similar known vanillin derivatives such as vanillin isobutyrate and ethylvanillin propionate, the ethylvanillin isobutyrate according to the invention is also attractive because of its greater tenacity, as a result of which the long-lastingness of corresponding perfume oils, when they are applied, for example, to the skin, is markedly extended, and because of its greater intensity (Tab. 1), which make it possible to develop perfume oils having a comparatively higher odoriferous strength or to achieve comparable effects in perfume oils using considerably lower dosages.

TABLE 1

Odoriferous intensity of vanillin isobutyrate and ethylvanillin isobutyrate and ethyl-vanillin propionate
Tests are carried out to ascertain the concentrations in diethyl phthalate which are still clearly perceptible by smell when applied to a blotter ("smelling strip"):

| Dilution | 1% by wt. | 0.1% by wt. | 0.01% by wt. |
|---|---|---|---|
| Vanillin isobutyrate | + | + | — |
| Ethylvanillin isobutyrate | + | + | + |
| Ethylvanillin propionate | + | + | — |

Compared with vanillin isobutyrate and ethylvanillin propionate, ethylvanillin isobutyrate also has significantly improved stability to light (see Tables 2 and 3), which is apparent from its lower tendency towards discoloration in light.

TABLE 2

Determination of the photostability of vanillin isobutyrate and ethylvanillin isobutyrate and ethylvanillin propionate during UV light irradiation [data in % of the starting concentration]

| | 0 | 2 h | 4 h | 8 h | 24 h | no irradiation (54 h) |
|---|---|---|---|---|---|---|
| Vanillin isobutyrate | 100 | 97 | 93 | 85 | 56 | 97 |
| Ethylvanillin isobutyrate | 100 | 100 | 98 | 91 | 71 | 100 |
| Ethylvanillin propionate | 100 | 99 | 98 | 91 | 72 | 91 |

Conditions: Wavelength: λ>290 nm; intensity: 40 watt/m$^2$; temperature 40° C.; concentration: 10% by weight in ethanol; colourless glass cuvettes.

Under these conditions, ethylvanillin propionate has a photostability comparable with that of ethylvanillin isobutyrate. If, however, the compounds are exposed to daylight for a prolonged period, ethylvanillin isobutyrate is clearly superior as regards stability to light.

TABLE 3

Determination of the stability to light of vanillin isobutyrate and ethylvanillin isobutyrate and ethylvanillin propionate during irradiation with daylight [data in % of the starting concentration]

| | 0 | 30 d | 90 d | no irradiation (90 d) |
|---|---|---|---|---|
| Vanillin isobutyrate | 100 | 80 | 30 | 95 |
| Ethylvanillin isobutyrate | 100 | 98 | 61 | 100 |
| Ethylvanillin propionate | 100 | 88 | 31 | 97 |

Conditions: 10% solutions in ethanol; colourless glass; diffuse daylight, room temperature.

The invention thus provides 3-ethoxy4-isobutyryloxy-benzaldehyde.

Ethylvanillin isobutyrate I is readily obtainable in a manner known per se by reacting ethylvanillin II with isobutyroyl chloride or isobutyric anhydride III.

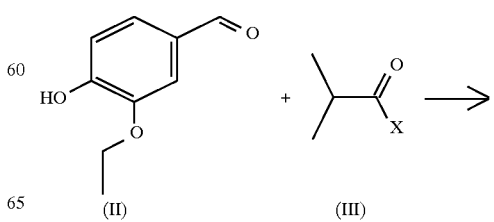

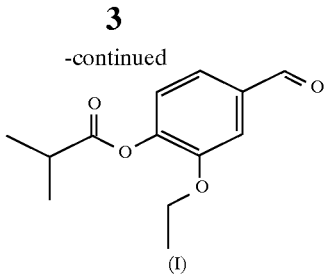

X = Cl or $-O-CO-CH(CH_3)_2$.

The III/II molar ratio can generally be from 1 to 3, preferably from 1.1 to 2, particularly from 1.1 to 1.5.

If isobutyroyl chloride is used as acylating agent, it is advantageous to work in the presence of an organic base, such as, for example, pyridine, alkyl-substituted pyridines, quinolines, tertiary amines, such as N,N-dimethylbenzylamine, triethylamine, tributylamine etc., in order to scavenge the hydrochloric acid liberated. The amount of base added is, in this connection, at least one equivalent, based on the isobutyroyl chloride used.

If isobutyric anhydride is used, it is not necessary to work in the presence of a basic compound, and the isobutyric acid liberated can be distilled off from the reaction mixture.

The reaction can be carried out in the presence or absence of an organic solvent which is inert under the reaction conditions. Examples of such solvents are aromatic compounds, such as benzene, toluene and xylenes, linear, branched and cyclic aliphatic compounds, such as benzine and cyclohexane, ethers, such as, for example, diethyl ether, ethylene glycol dimethyl ether, diethylene glycol dimethyl ether, tetrahydrofuran, dioxane and tert.-butyl methyl ether, and also linear and cyclic acid amides, such as, for example, dimethylformamide and N-methylpyrrolidone.

The reaction temperature can be from 0° to 180° C., preferably from 20 to 140° C. The progress of the reaction can be monitored by usual methods, for example using thin-layer chromatography. At the end of the reaction, excess III can be distilled off, if necessary neutralized using a base, such as sodium hydroxide solution, aqueous solutions of sodium carbonate or bicarbonate, the organic phase can, if required, be dried and the reaction product can be purified by distillation or recrystallization.

Thus, the invention further provides a process for preparing ethylvanillin isobutyrate by reacting ethylvanillin with a reactive isobutyric acid derivative.

Because of its excellent organoleptic properties, ethylvanillin isobutyrate is especially suitable for use in perfume and flavour compositions. It can be very easily combined with other fragrances and flavour substances in different, varying quantity ratios to give novel perfume and flavour compositions. In perfume compositions the quantity used is from 0.1 to 20% by weight, preferably from 0.5 to 10% by weight, based on the total composition.

Such perfume compositions can be used not only in alcoholic solution as fine perfumes, but also for perfuming cosmetics, for example creams, lotions, aerosols, toilet soaps etc., household products such as cleaners and laundry detergents, fabric softeners, disinfectants and textile treatment agents, and other industrial products, the quantity of the perfume composition being from 0.1 to 40% by weight, preferably from 0.5 to 20% by weight, based on the total product.

In flavour compositions the quantity of the compound according to the invention used is from 0.1 to 50% by weight, preferably from 2 to 10% by weight, based on the total composition. Such flavour compositions can be used in the entire foodstuffs and luxury products sector. They are particularly suitable for flavouring fatty products, bakery products, yoghurt, ice cream, sweets, alcoholic and nonalcoholic drinks, tobacco and substances used in the manufacture of tobacco products. The dosage of such flavour compositions is from 0.0005 to 0.05% by weight, preferably from 0.001 to 0.01% by weight, based on the finished product. In tobacco, the dosage of the compound according to the invention is from 0.005 to 0.5% by weight, preferably from 0.01 to 0.1% by weight, based on tobacco.

The invention also thus provides for the use of ethylvanillin isobutyrate as a fragrance and flavour substance.

The percentages in the following examples refer in each case to the weight; parts are parts by weight.

EXAMPLE 1

Preparation of ethylvanillin isobutyrate a) by reacting ethylvanillin with isobutyroyl chloride:

166 g (1 mol) of ethylvanillin and 160 g (1.33 mol) of N,N-dimethylbenzylamine are introduced into 800 ml of tert-butyl methyl ether in a stirred apparatus with the exclusion of moisture. 128 g (1.2 mol) of isobutyroyl chloride are added over the course of 1.5 h, during which the reaction temperature rises to about 38° C. The reaction mixture is stirred overnight at room temperature and then poured into about 1 l of water. The organic phase is separated off, washed with hydrochloric acid, 5% sodium hydroxide solution and water, dried and evaporated, giving a residue of 238 g of crude ethylvanillin isobutyrate, which is recrystallized from 240 ml of isopropanol. Yield 215 g of ethylvanillin isobutyrate; m.p. 57° C.

MS:$M^+$ =236 (9);m/e=166 (90), 138 (50), 137 (61), 109 (13), 81 (20), 71 (36), 51(15), 43 (100), 41 (24), 27 (25).

$^1$H-NMR (200 MHz,$CDCl_3$):1.34(d,J=7.0 Hz, 6 H),1.41 (t,J=7.0 Hz, 3 H),2.86(sep,J=7.0 Hz,1 H),4.12(q,J=7.0 Hz,2 H),7.1–8.0(m,3 H),9,94(s,1 H)δppm.

$^{13}$C-NMR(90 MHz,$CDCl_3$):15, 19, 34, 64, 111, 123, 125, 135, 145, 151, 175, 191 δppm.

b) by reacting ethylvanillin with isobutyric anhydride:

166 g of ethylvanillin are introduced into a 500 ml three-neck flask fitted with a 30 cm packed column and melted, and 189.6 g of isobutyric anhydride are added at a maximum temperature of 100° C. The reaction is only slightly exothermic. When addition is complete, the isobutyric acid can firstly be distilled off at a still temperature of 120° C. and 150 mbar, and iso-butyric acid and excess anhydride can finally be distilled at up to 130° C. and 20 mbar. The system is allowed to cool to 90° C., 500 ml of isopropanol are added and crystallization takes place upon further stirring and cooling to 7° C. The crystals are filtered off with suction, washed twice with 60 ml of cold isopropanol and dried, giving 182 g of ethylvanillin isobutyrate. Repeated crystallization from the mother liquor produces another 22.8 g of ethylvanillin isobutyrate.

EXAMPLE 2

Preparation of perfumes using ethylvanillin isobutyrate a) Preparation of an artificial vanilla extract for use in perfume oils:

A mixture is prepared from:
Furaneol, 0.15% in isopropyl myristate 7 g
Damascon beta, 1% in benzyl alcohol 0.6 g Damascon alpha, 1% in benzyl alcohol 0.4 g
Guaiacol, 10% in isopropyl myristate 3 g
Peruvian balsam oil 3 g
Tolu resin, 50% in benzyl benzoate 15 g
Benzoin resin, 50% in benzyl benzoate 7 g
Tree moss absolute, 50% in triethyl citrate 40 g
Vanillin 440 g
Benzyl alcohol 984 g Replacing 100 g of the benzyl alcohol used with the same amount of ethylvanillin isobutyrate gives this composition a delicate fruity-chocolatey note, resulting in the odour impression of natural vanilla extract.

b) Preparation of a perfume having an oriental note:

A mixture is prepared from:
Vertocitral H&R 2 g
Isoananat H&R 5 g
Bergamot oil, dist. colourless 100 g
Mandarin oil 50 g
Y-Octalactone 5 g
Profarnesol H&R 10 g
Linalool 150 g
Phenoxanol® IFF 50 g
Rosaphen H&R 100 g
Hedion® Firmenich 200 g
cis-3-Hexenyl salicylate 13 g
Coumarin 10 g
Hexahydroiraldein H&R 20 g
Boisanol H&R 100 g
Sandolen H&R 30 g
Indole, 10% in dipropylene glycol 5 g For comparison, either 10 g of vanillin in 140 g of dipropylene glycol or 50 g of ethylvanillin isobutyrate in 100 g of dipropylene glycol are added to the mixture. The composition containing ethylvanillin isobutyrate has a more delicate, slightly fruity-chocolatey fragrance, becomes richer and more valuable as a result of the vanilla extract note and, overall, acquires volume and elegance.

EXAMPLE 3

Preparation of a flavour mixture having a vanilla extract character, which can, for example, be used in ice cream or sweets, using ethylvanillin isobutyrate.

A mixture is prepared from:

| | |
|---|---|
| Dihydrocoumarin | 1 |
| Decalactone, delta- | 1 |
| Diacetyl, 10% in propylene glycol | 1 |
| Guaiacol | 1 |
| Heliotropin | 10 |
| Ethylvanillin | 50 |
| Vanillin | 200 |
| Propylene glycol | 736 |
| | 1000 |

By adding 20 to 100 parts of ethylvanillin isobutyrate, or by replacing the ethylvanillin with ethylvanillin isobutyrate, the taste pattern of the vanilla aroma becomes fuller, sweeter and more harmonious and the whole flavour takes on a much more natural vanilla note which approaches real vanilla extract.

We claim:
1. 3-Ethoxy-4-isobutyryloxy-benzaldehyde.
2. A process for preparing 3-ethoxy4-isobutyryloxy-benzaldehyde which comprises reacting 3-ethoxy4-hydroxy-benzaldehyde with a reactive isobutyric acid derivative.
3. The process of claim 2, wherein said reactive isobutyric acid derivative is isobutyroyl chloride or isobutyric anhydride.
4. A fragrance composition comprising a carrier and 3-ethoxy-4-isobutyryloxy-benzaldehyde.
5. The fragrance composition of claim 4, comprising 0.1 to 20% by weight, based on the total weight of the composition, of 3-ethoxy4-isobutyryloxy-benzaldehyde.
6. The fragrance composition of claim 4, wherein said carrier is alcohol.
7. A flavor composition comprising an edible carrier and 3-ethoxy4-isobutyryloxy-benzaldehyde.
8. The flavor composition of claim 7, comprising 0.1 to 50% by weight, based on the total weight of the composition, of 3-ethoxy-4-isobutyryloxy-benzaldehyde.
9. The flavor composition of claim 8, comprising 2 to 10% by weight, based on the total weight of the composition, of 3-ethoxy4-isobutyryloxy-benzaldehyde.
10. The flavor composition of claim 7, wherein said edible carrier is a fatty food product, yoghurt, ice cream, sweet, alcoholic drink, non-alcoholic drink, or tobacco product.

* * * * *

UNITED STATES PATENT AND TRADEMARK OFFICE
CERTIFICATE OF CORRECTION

PATENT NO. :   5,874,398
DATED      :   February 23, 1999
INVENTOR(S):   Horst Surburg et al.

It is certified that error appears in the above-identified patent and that said Letters Patent is hereby corrected as shown below:

In claim 2, lines 1-2, after "ethoxy" please insert a hyphen -----.

In claim 5, line 3, after "ethoxy" please insert a hyphen -----.

In claim 7, line 2, after "ethoxy" please insert a hyphen -----.

In claim 9, line 3, after "ethoxy" please insert a hyphen -----.

Signed and Sealed this

Tenth Day of April, 2001

Attest:

NICHOLAS P. GODICI

Attesting Officer        Acting Director of the United States Patent and Trademark Office